(12) United States Patent
Kim et al.

(10) Patent No.: US 10,066,031 B1
(45) Date of Patent: Sep. 4, 2018

(54) METHOD OF SEPARATING ETHYLENE OLIGOMERIZATION REACTOR EFFLUENT

(71) Applicant: LG CHEM, LTD., Seoul (KR)

(72) Inventors: Eun-Kyo Kim, Daejeon (KR); Jong-Ku Lee, Daejeon (KR); Jeong-Seok Lee, Daejeon (KR); Mi-Kyung Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/527,179

(22) PCT Filed: Oct. 11, 2016

(86) PCT No.: PCT/KR2016/011371
§ 371 (c)(1),
(2) Date: May 16, 2017

(87) PCT Pub. No.: WO2017/069446
PCT Pub. Date: Apr. 27, 2017

(30) Foreign Application Priority Data

Oct. 19, 2015 (KR) .......................... 10-2015-0145231

(51) Int. Cl.
| | | |
|---|---|---|
| C08F 2/00 | (2006.01) | |
| C08F 210/00 | (2006.01) | |
| C08F 6/00 | (2006.01) | |
| B01D 3/14 | (2006.01) | |
| C07C 2/08 | (2006.01) | |
| C07C 11/02 | (2006.01) | |
| C08F 10/02 | (2006.01) | |

(52) U.S. Cl.
CPC .............. *C08F 6/001* (2013.01); *B01D 3/143* (2013.01); *C07C 2/08* (2013.01); *C07C 11/02* (2013.01); *B01D 2256/24* (2013.01); *B01D 2257/702* (2013.01); *C08F 10/02* (2013.01); *C08F 2500/02* (2013.01)

(58) Field of Classification Search
CPC ............ C07C 7/00; C07C 7/10; C07C 11/107
USPC ..................................... 526/63, 348
See application file for complete search history.

(56) References Cited

U.S. PATENT DOCUMENTS

| | | |
|---|---|---|
| 5,853,551 A | 12/1998 | Boucot et al. |
| 2011/0046425 A1 | 2/2011 | Gartside |
| 2011/0130604 A1* | 6/2011 | Gartside ................ B01D 3/146 585/324 |
| 2015/0299069 A1 | 10/2015 | Azam |

FOREIGN PATENT DOCUMENTS

| | | |
|---|---|---|
| EP | 0 397 273 A2 | 11/1990 |
| JP | 61-90703 A | 5/1986 |
| JP | 2009-120588 A | 6/2009 |
| JP | 2015-074617 A | 4/2015 |
| KR | 2010-0134725 A | 12/2010 |
| KR | 2015-0088249 A | 7/2015 |
| WO | 2014-082689 A | 6/2014 |
| WO | 2014/202715 A1 | 12/2014 |

* cited by examiner

*Primary Examiner* — William K Cheung
(74) *Attorney, Agent, or Firm* — Dentons US LLP

(57) ABSTRACT

Disclosed is a method of separating an ethylene oligomerization effluent, in which, during the separation and purification of a product obtained through ethylene oligomerization, the temperature of the reaction product is adjusted and used, thus improving energy efficiency.

12 Claims, 3 Drawing Sheets

METHOD OF SEPARATING ETHYLENE OLIGOMERIZATION REACTOR EFFLUENT

TECHNICAL FIELD

This application is a National Stage Entry of International Application No. PCT/KR2016/011371 filed on Oct. 11, 2016, which claims priority to and the benefit of Korean Patent Application No. 10-2015-0145231, filed Oct. 19, 2015, which is hereby incorporated by reference in its entirety into this application.

The present invention relates to a method of separating an ethylene oligomerization effluent, and more particularly to a method of separating an ethylene oligomerization effluent, in which, during the separation and purification of a product obtained through ethylene oligomerization, the temperature of the reaction product is adjusted and used to thus improve energy efficiency.

BACKGROUND ART

A reaction product, obtained through ethylene polymerization, is composed of unreacted ethylene, a solvent necessary to dissolve a catalyst and ethylene upon polymerization, and linear α-olefins having various numbers of carbon atoms polymerized through the reaction, and such an effluent stream (reaction product) is separated into a target product via multiple recovery towers. FIG. 1 shows a typical process of separating an ethylene polymerization effluent. As shown in FIG. 1, the effluent stream is separated and purified by being passed through an unreacted ethylene separation tower (not shown), a C4 separation tower 2 (or a butane separation tower) and then a C6 separation tower 4 (or a 1-hexene recovery tower). Here, the bottom liquid discharged from the bottom of the C4 separation tower 2 is supplied as a feed for the C6 separation tower 4, and the temperature of the feed stream is higher than the temperature of the tray positioned at the bottom of the C6 separation tower 4, and thus a load is applied to a condenser 6 connected to the C6 separation tower 4, ultimately increasing energy consumption and associated costs. That is, since the temperature of the feed introduced into the C6 separation tower 4 is higher than the temperature of the tower itself, an excessive load is applied to the condenser 6. Hence, to remove heat in order to solve such problems, a utility such as cooling water is excessively used, thus increasing operating costs.

Meanwhile, using the high temperature of the feed, the feed may be supplied to a tray located lower than the tray of the C6 separation tower 4 to which the feed is originally supplied, in order to solve the above problems. In this case, however, the composition distribution in the tower is affected, and thus limitations are imposed on improving energy efficiency by controlling the feed stage of the tower to which the feed is supplied. Therefore, with the goal of solving the above problems, a method of efficiently separating effluents produced through ethylene polymerization using a small amount of energy is required.

DISCLOSURE

Technical Problem

Accordingly, the present invention is intended to provide a method of separating an ethylene oligomerization effluent, in which, during the separation and purification of a product obtained through ethylene oligomerization, the reaction product is cooled to thus reduce the load on a condenser, thereby decreasing the use of energy.

In addition, the present invention is intended to provide a method of separating an ethylene oligomerization effluent, in which heat generated by cooling the reaction product may be supplied to a reboiler and utilized, thus improving energy efficiency.

Technical Solution

Therefore, the present invention provides a method of separating an ethylene oligomerization effluent, suitable for use in the separation and purification of a product obtained through ethylene polymerization, the method comprising: cooling a residual reaction product, which is discharged from a C2/C4 separation tower for separating both unreacted ethylene and 1-butene of a reaction product or a C4 separation tower for separating only 1-butene and is supplied as a feed for a C6 separation tower; and sequentially transferring the cooled residual reaction product to the C6 separation tower, a solvent separation tower, a C8 separation tower and a C10 separation tower, wherein heat generated by cooling the reaction product discharged from the C2/C4 separation tower or the C4 separation tower is supplied to a reboiler of the C6 separation tower and thus used.

Advantageous Effects

According to the present invention, a method of separating an ethylene oligomerization effluent, suitable for use in the separation and purification of a product obtained through ethylene oligomerization, enables the reaction product to be cooled to thus reduce a load on a condenser, thereby decreasing the use of energy. Furthermore, heat generated by cooling the reaction product can be supplied to a reboiler and thus utilized, thereby improving energy efficiency.

BEST MODE

Hereinafter, a detailed description will be given of the present invention, with reference to the appended drawings.

Figure 2:
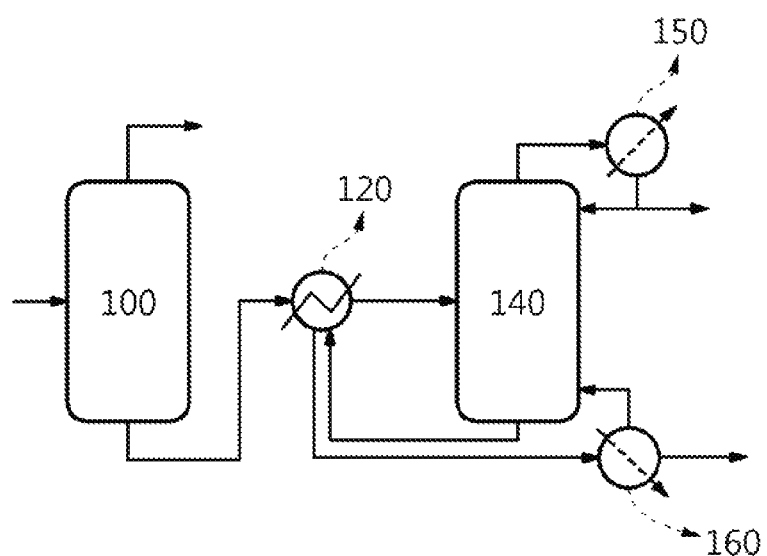
FIG. 2 shows a process of separating an ethylene oligomerization effluent according to an embodiment of the present invention.

FIG. 2 shows the process of separating an ethylene oligomerization effluent according to an embodiment of the present invention. With reference to FIG. 2, the method of separating the ethylene oligomerization effluent according to the present invention, suitable for use in the separation and purification of a product obtained through ethylene polymerization, includes cooling a residual reaction product, which is discharged from a C2/C4 separation tower (not shown) for separating both unreacted ethylene and 1-butene of a reaction product or a C4 separation tower 100 for separating only 1-butene and is supplied as a feed for a C6 separation tower 140, and sequentially transferring the cooled residual reaction product to the C6 separation tower 140, a solvent separation tower (not shown), a C8 separation tower (not shown) and a C10 separation tower (not shown), wherein heat (cooling heat) generated by cooling the reaction product discharged from the C2/C4 separation tower (not shown) or the C4 separation tower 100 is supplied to a reboiler 160 of the C6 separation tower 140, thereby using the heat.

As for the present invention, in order to selectively prepare an oligomer, such as 1-hexene and 1-octene, ethylene polymerization has to be initiated using a chromium (Cr)- or a titanium (Ti)-based catalyst, and the reaction product (bottom liquid) discharged from the C4 separation tower 100, namely the residual reaction product excluding a C4 mixture including unreacted ethylene and 1-butene, may include not only a linear α-olefin having 6 or more carbon atoms produced through ethylene polymerization, for example, a C6 mixture such as 1-hexene and so on, a C8 mixture such as 1-octene and so on, and a C10 mixture such as 1-decene and so on, but also a mixture having 12 or more carbon atoms depending on the polymerization conditions, and may also include a solvent for dissolving ethylene and the catalyst upon polymerization. Thus, the method of separating the ethylene oligomerization effluent according to the present invention may further include sequentially transferring the reaction product passed through the C10 separation tower (not shown) to an α-olefin separation tower (not shown) for separating an α-olefin having 12 or more carbon atoms produced through ethylene polymerization, as necessary.

Meanwhile, in the present invention, C of C4, C6, C8 and C10 indicates carbon, and C6 indicates 6 carbon atoms, and a mixture thereof is a polymer produced through ethylene polymerization. In the present invention, α-olefin produced through ethylene polymerization is an oligomer having 4 to 40 carbon atoms, and preferably 4 to 10 carbon atoms, and examples thereof may include an ethylene dimer having 4 carbon atoms, an ethylene trimer having 6 carbon atoms, and an ethylene tetramer having 8 carbon atoms, and the α-olefin has a molecular weight of 1,500 or less, and preferably 1,000 or less.

The temperature of the reaction product (bottom liquid) discharged from the C4 separation tower 100, namely the reaction product that is supplied as a feed for the C6 separation tower 140, typically exceeds 200° C. (e.g. the temperature of the bottom liquid discharged from the C4 separation tower 100 in FIG. 2 is 235° C.), and is thus higher than the temperature of the tray located at the bottom of the C6 separation tower 140, and thus a load is applied to the condenser 150 connected to the C6 separation tower 140, ultimately increasing energy consumption and related expense.

Accordingly, in the present invention, as shown in FIG. 2, a heat exchanger 120 is provided in the reboiler 160 connected to the C6 separation tower 140 while being located between the C2/C4 separation tower (not shown) or the C4 separation tower 100 and the C6 separation tower 140, whereby the temperature of the reaction product supplied as the feed for the C6 separation tower 140 is decreased (that is, the residual reaction product excluding unreacted ethylene and 1-butene is cooled), whereby a load on the condenser 150 connected to the C6 separation tower 140 is reduced, and also, the operating costs consumed in order to remove heat may be decreased. The temperature of the cooled reaction product is preferably adjusted to be similar to the temperature of the tray for supplying the feed to the C6 separation tower 140, and may vary depending on the processing conditions, but may be set in the range of 50 to 200° C.

As mentioned above, in the present invention, the member for decreasing the temperature of the reaction product supplied as the feed for the C6 separation tower 140 is exemplified by the heat exchanger 120. To more efficiently remove heat, a small amount of utility that enables cooling, such as cooling water, may be used together with the heat exchanger 120.

In the present invention, cooling heat, generated by lowering the temperature of the reaction product supplied as the feed for the C6 separation tower 140, is supplied to the reboiler 160 of the C6 separation tower 140 and thus used, whereby a heat source (hot utility or steam) conventionally supplied to a reboiler may not be used or may be used in only a small amount, thus increasing energy efficiency.

Heat (cooling heat) supplied to the reboiler 160 of the C6 separation tower 140 is generated from the heat exchanger 120 provided in the reboiler 160. More specifically, such heat is generated through heat exchange between the feed supplied to the C6 separation tower 140 from the C4 separation tower 100 and the stream transferred to the reboiler 160 from the C6 separation tower 140 so as to achieve reheating. That is, the feed supplied to the C6 separation tower 140 is cooled, and simultaneously heat lost from the feed is used for the reboiler 160.

In order to operate the C6 separation tower 140 in an energy-efficient manner, the amount of heat supplied from the reboiler 160 connected to the bottom or the side of the C6 separation tower 140 has to be similar to the amount of heat that is removed from the condenser 150 connected to the top of the C6 separation tower 140. If the amount of heat supplied to the reboiler 160 is not sufficient, a hot utility including steam, conventionally useful as a heat source of a reboiler, may be used to enable additional heat supply.

Figure 3:
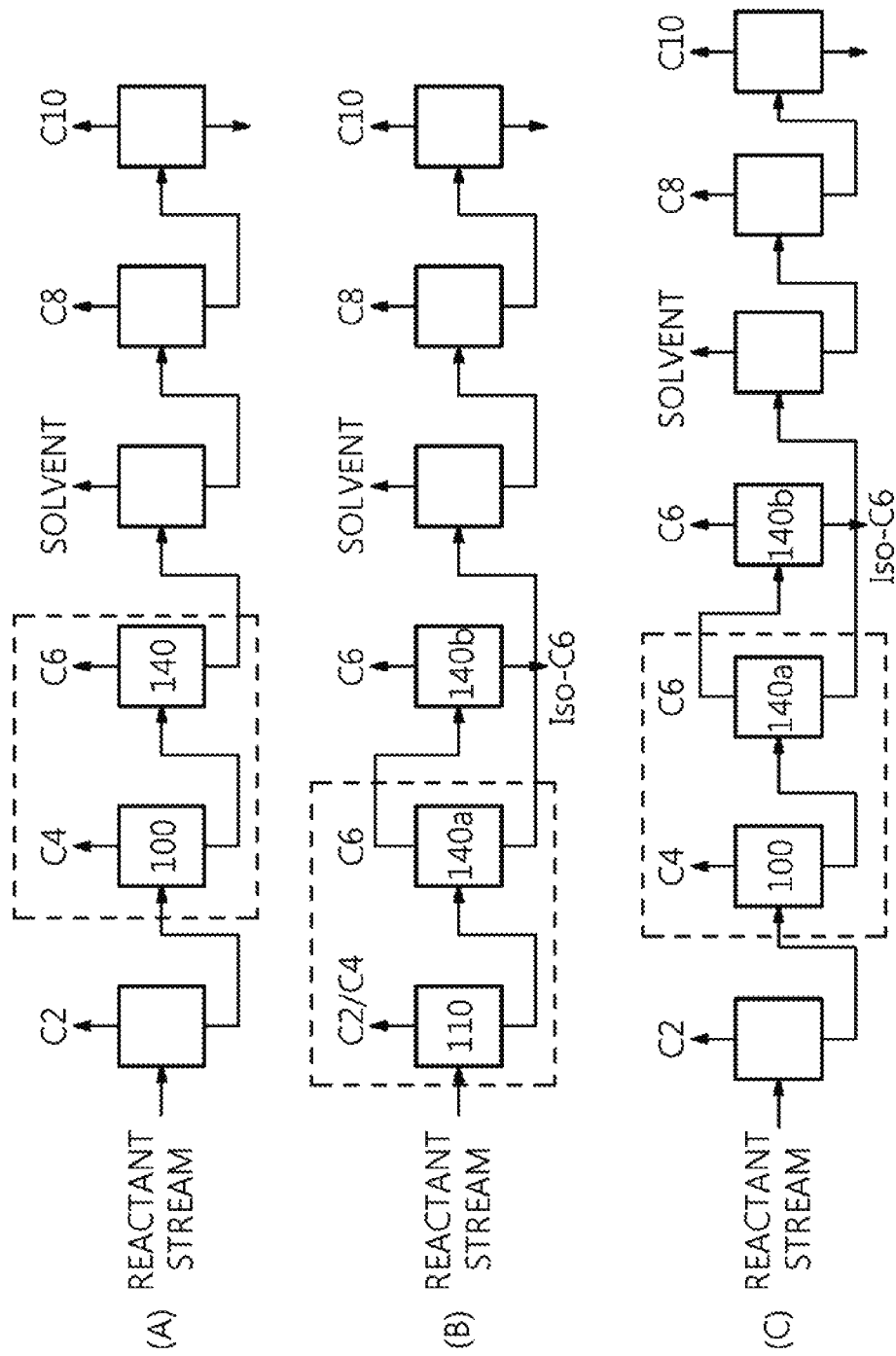
FIG. 3 schematically shows various types of ethylene oligomerization effluent separation procedures to which the process of separating the ethylene oligomerization effluent according to the present invention can be applied.

The method of separating the ethylene oligomerization effluent according to the present invention may be applied to various types of ethylene oligomerization effluent separation procedures. FIG. 3 schematically shows various types of ethylene oligomerization effluent separation procedures to which the process of separating the ethylene oligomerization effluent according to the present invention may be applied, wherein A of FIG. 3 shows the connection of a C4 separation tower 100 to a single C6 separation tower 140, B of FIG. 3 shows the connection of a C2/C4 separation tower 110 to a first C6 separation tower 140a and the connection of the first C6 separation tower 140a to a second C6 separation tower 140b, and C of FIG. 3 shows the connection of a C4 separation tower 100 to a first C6 separation tower 140a and the connection of the first C6 separation tower 140a to a second C6 separation tower 140b. Here, the first C6 separation tower 140a of FIGS. 3-B and 3-C is used to separate C6 and the solvent, and is responsible for the same function as in the C6 separation tower 140 of FIG. 3-A, and the second C6 separation tower 140b of FIGS. 3-B and 3-C is an additional separation tower for additionally separating isomers by purifying once more a C6 stream discharged from the top of the first C6 separation tower 140a when C6 having desired purity cannot be obtained from the first C6 separation tower 140a.

In this way, the method of separating the ethylene oligomerization effluent according to the present invention may be applied to most of the processes of separating the ethylene oligomerization effluent including the procedures of FIG. 3 (in each of A to C of FIG. 3, it may be applied to the portions represented by the blue dotted lines). As shown in FIG. 3, the reaction product, which is discharged from the C4 separation tower 100 or the C2/C4 separation tower 110 and is supplied as the feed for the C6 separation tower 140 or the first C6 separation tower 140a, is cooled, and heat generated through cooling is used as the heat source of the reboiler (not shown) connected to the C6 separation tower 140 or the first C6 separation tower 140a, thus reducing energy consumption.

When using the method of separating the ethylene oligomerization effluent according to the present invention, the amount of energy that is consumed by the condenser 150 connected to the C6 separation tower 140 may be reduced, and also, the amount of utility such as cooling water or a heat source conventionally used for the condenser 150 and the reboiler 160 may be decreased, thus lowering the operating cost. Furthermore, the thermal energy of the feed is utilized in the reboiler 160, thereby maximizing the energy efficiency in the processing. Even when the same amount of energy is used, the purity (quality) of products may be increased compared to conventional cases.

MODE FOR INVENTION

A better understanding of the present invention may be obtained via the following examples, which are merely set forth to illustrate the present invention, and such examples may be variously modified and altered within the scope and spirit of the invention, as will be apparent to those skilled in the art, and such modifications and alterations should also be understood as falling within the scope defined by the accompanying claims.

[Example 1] Separation of Ethylene Oligomerization Effluent

With reference to FIG. 2 or A of FIG. 3, a Cr-based catalyst, an ethylene monomer and a solvent for dissolving them were added so that polymerization occurred. Of the reaction product, unreacted ethylene was separated from the C2 separation tower, and a C4 mixture was separated from the C4 separation tower 100, and the residual reaction product was transferred to the next stage. Here, the residual reaction product (including an ethylene polymer having 6 or more carbon atoms and solvent) had a pressure of 18.60 bar and a temperature of 235° C., and in order to lower the temperature thereof before being supplied to the C6 separation tower 140, heat exchange with the bottom stream of the C6 separation tower 140 was performed using a heat exchanger 120 in the reboiler. Subsequently, the residual reaction product cooled to 142° C. was sequentially transferred to the C6 separation tower 140, a solvent separation tower, a C8 separation tower and a C10 separation tower, thus separating ethylene oligomers depending on the number of carbon atoms and obtaining products thereof.

[Comparative Example 1] Separation of Ethylene Oligomerization Effluent

Figure 1:
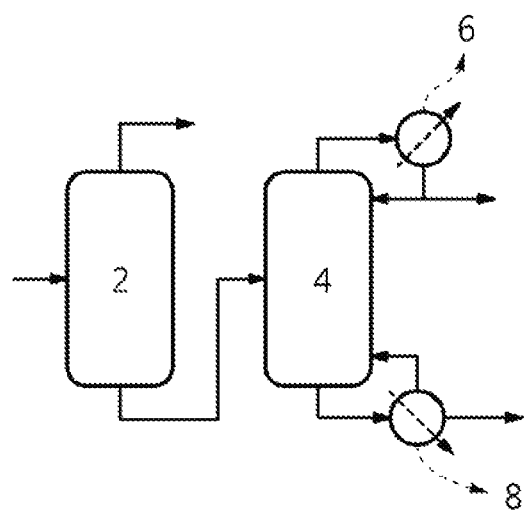
FIG. 1 shows a typical process of separating an ethylene polymerization effluent.

As shown in FIG. 1, ethylene oligomers were separated depending on the number of carbon atoms and produced in the same manner as in Example 1, with the exception that the heat exchanger for cooling the residual reaction product transferred from the C4 separation tower 2 and supplying the cooling heat to the reboiler 8 of the C6 separation tower 4 was not used.

[Example 1 and Comparative Example 1] Evaluation of Energy Efficiency in Separation of Ethylene Oligomerization Effluent In Example 1 and Comparative Example 1, the effluents obtained through ethylene polymerization were separated, after which the amounts of energy used in the condenser and the reboiler connected to the C6 separation tower were measured. The results are shown in Table 1 below. The feeds supplied to the C6 separation tower in Example 1 and Comparative Example 1 had the same composition (i.e. the same feed stream composition).

TABLE 11

| | | Example 1 | | Comp. Example 1 | |
|---|---|---|---|---|---|
| Energy source and amount thereof | Condenser | −2.32 Gcal/hr | Use of utility | −3.67 Gcal/hr | Use of utility |
| | Reboiler | 1.97 Gcal/hr | 1.61 Gcal/hr | Use of feed cooling heat | 1.71 Gcal/hr | Use of utility |
| | | | 0.36 Gcal/hr | Use of utility | | |
| Temperature of feed supplied to C6 separation tower | | 142° C. | | 235° C. | |

Based on the results of measurement of the amounts of energy used for the condenser and the reboiler connected to the C6 separation tower, as is apparent from Table 1, in Example 1, in which the heat exchanger was used and thus the residual reaction product transferred from the C4 separation tower to the C6 separation tower was cooled and the cooling heat was supplied to the reboiler, the amount of energy used in the condenser was decreased by about 37% compared to Comparative Example 1, in which a heat exchanger was not used (−3.67 Gcal/hr→−2.32 Gcal/hr). Hence, the feed (reaction product) supplied to the C6 separation tower is cooled and the temperature thereof is lowered, thereby reducing the load on the condenser.

Also, in Example 1, which uses cooling heat generated by cooling the residual reaction product as the main energy source of the reboiler, the amount of energy of hot utility (e.g. steam) used in the reboiler, in addition to the cooling heat, was decreased by about 79% compared to Comparative Example 1, which uses only the hot utility without the use of the heat exchanger (1.71 Gcal/hr→0.36 Gcal/hr). Accordingly, even when the total amount of energy used in the reboiler is higher in Example 1 than in Comparative Example 1, most energy used in the reboiler in Example 1 is obtained using cooling heat generated by cooling the residual reaction product, thus increasing energy efficiency somewhat.

The invention claimed is:

1. A method of separating an ethylene oligomerization effluent, suitable for use in separation and purification of a product obtained through ethylene polymerization, the method comprising:
    cooling a residual reaction product, which is discharged from a C2/C4 separation tower for separating both unreacted ethylene and 1-butene of a reaction product or a C4 separation tower for separating 1-butene and is supplied as a feed for a C6 separation tower; and
    sequentially transferring the cooled residual reaction product to the C6 separation tower, a solvent separation tower, a C8 separation tower and a C10 separation tower,
    wherein heat generated by cooling the reaction product discharged from the C2/C4 separation tower or the C4 separation tower is supplied to a reboiler of the C6 separation tower and thus used.

2. The method of claim 1, wherein the residual reaction product, excluding the unreacted ethylene and 1-butene, is cooled by a heat exchanger that is included in the reboiler connected to the C6 separation tower while being located between the C2/C4 separation tower or the C4 separation tower and the C6 separation tower.

3. The method of claim 1, wherein a temperature of the cooled reaction product is adjusted to be similar to a temperature of a tray of the C6 separation tower to which a feed is supplied.

4. The method of claim 1, wherein a temperature of the cooled reaction product ranges from 50 to 200° C.

5. The method of claim 1, wherein the cooling the reaction product is performed using both a heat exchanger and a utility that enables cooling.

6. The method of claim 1, wherein heat supplied to the reboiler of the C6 separation tower is generated through heat exchange between a feed supplied to the C6 separation tower from the C4 separation tower and a stream transferred to the reboiler from the C6 separation tower so as to achieve reheating.

7. The method of claim 1, wherein when an amount of heat supplied to the reboiler is not sufficient, a hot utility including steam is additionally used.

8. The method of claim 1, wherein the reaction product discharged from the C4 separation tower includes a linear α-olefin having 6 or more carbon atoms and a solvent used to dissolve ethylene and a catalyst upon polymerization.

9. The method of claim 8, wherein the linear α-olefin having 6 or more carbon atoms includes 1-hexene, 1-octene and 1-decene.

10. The method of claim 1, further comprising sequentially transferring the reaction product passed through the C10 separation tower to an α-olefin separation tower for separating an α-olefin having 12 or more carbon atoms produced through ethylene polymerization.

11. The method of claim 1, wherein an α-olefin produced through the ethylene polymerization is an oligomer having 4 to 40 carbon atoms.

12. The method of claim 11, wherein the α-olefin has a molecular weight of 1,500 or less.

* * * * *